United States Patent
Miguirditchian et al.

(10) Patent No.: US 10,252,983 B2
(45) Date of Patent: Apr. 9, 2019

(54) DISSYMMETRIC N,N-DIALKYLAMIDES, THE SYNTHESIS THEREOF AND USES OF SAME

(71) Applicants: COMMISSARIAT A L'ENERGIE ATOMIQUE ET AUX ENERGIES ALTERNATIVES, Paris (FR); AREVA NC, Courbevoie (FR)

(72) Inventors: Manuel Miguirditchian, Avignon (FR); Pascal Baron, Bagnols sur Ceze (FR); Sandra Lopes Moreira, Nantes (FR); Gaëlle Milanole, Orange (FR); Cécile Marie, Avignon (FR)

(73) Assignees: COMMISSARIAT A L'ENERGIE ATOMIQUE ET AUX ENERGIES ALTERNATIVES, Paris (FR); ORANO CYCLE, Courbevoie (FR)

( * ) Notice: Subject to any disclaimer, the term of this patent is extended or adjusted under 35 U.S.C. 154(b) by 0 days.

(21) Appl. No.: 15/748,030

(22) PCT Filed: Jul. 28, 2016

(86) PCT No.: PCT/EP2016/068016
§ 371 (c)(1),
(2) Date: Jan. 26, 2018

(87) PCT Pub. No.: WO2017/017193
PCT Pub. Date: Feb. 2, 2017

(65) Prior Publication Data
US 2018/0222849 A1    Aug. 9, 2018

(30) Foreign Application Priority Data

Jul. 29, 2015    (FR) ...................... 15 57264

(51) Int. Cl.
| | |
|---|---|
| *C07C 233/00* | (2006.01) |
| *C07C 233/05* | (2006.01) |
| *C22B 3/32* | (2006.01) |
| *C22B 60/02* | (2006.01) |
| *C22B 60/04* | (2006.01) |
| *C07C 231/02* | (2006.01) |

(52) U.S. Cl.
CPC .......... *C07C 233/05* (2013.01); *C07C 231/02* (2013.01); *C22B 3/0024* (2013.01); *C22B 60/026* (2013.01); *C22B 60/0239* (2013.01); *C22B 60/04* (2013.01); *Y02P 10/234* (2015.11)

(58) Field of Classification Search
CPC ... C07C 233/05; C07C 231/02; C22B 3/0024; C22B 60/026; C22B 60/0239; C22B 60/04; G21C 19/46; Y02W 30/883
USPC .......................................................... 423/9
See application file for complete search history.

(56) References Cited

U.S. PATENT DOCUMENTS

| | | | |
|---|---|---|---|
| 4,772,429 A | 9/1988 | Descouls et al. | |
| 5,132,092 A | 7/1992 | Musikas et al. | |
| 7,887,767 B2 | 2/2011 | Baron et al. | |
| 8,394,346 B2 | 3/2013 | Emin et al. | |
| 8,795,610 B2 | 8/2014 | Saudray et al. | |
| 8,795,611 B2* | 8/2014 | Miguirditchian ..... | C22B 3/0024 423/9 |
| 9,074,266 B2 | 7/2015 | Bisson et al. | |

(Continued)

FOREIGN PATENT DOCUMENTS

| | | | |
|---|---|---|---|
| FR | 2 591 213 A1 | 6/1987 | |
| FR | 2 642 561 A1 | 8/1990 | |
| FR | 2 642 562 A1 | 8/1990 | |

OTHER PUBLICATIONS

International Search Report for PCT/EP2016/068016 dated Oct. 4, 2016.

(Continued)

*Primary Examiner* — Steven J Bos
(74) *Attorney, Agent, or Firm* — Pearne & Gordon LLP

(57) ABSTRACT

Novel dissymmetric N,N-dialkylamides which meet the following formula (I):

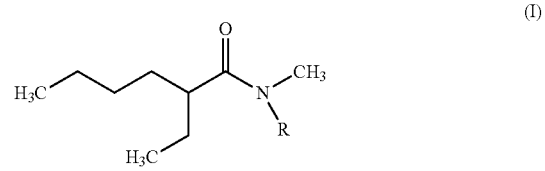

(I)

where R represents a linear or branched alkyl group at $C_8$ to $C_{15}$. A method for synthesizing these N,N-dialkylamides, and to the uses of same as extractants, alone or in admixture, in order to extract uranium and/or plutonium from an aqueous acid solution, or to totally or separate uranium from plutonium from an aqueous acid solution and, in particular, an aqueous solution resulting from dissolving spent nuclear fuel in nitric acid. Further, a method for processing an aqueous solution resulting from the dissolution of a spent nuclear fuel in nitric acid, allowing the uranium and plutonium contained in the solution to be extracted, separated and decontaminated in a single cycle, without requiring any plutonium reduction operation, and in which one of the aforementioned N,N-dialkylamides or a mixture of same is used as extractant. Applications for the method include the processing of spent nuclear fuels, in particular comprising uranium (e.g. UOX) or uranium and plutonium (e.g. MOX).

20 Claims, 2 Drawing Sheets

(56) References Cited

U.S. PATENT DOCUMENTS

2013/0202501 A1* 8/2013 Saudray ................. C22B 3/065
                                                              423/10
2016/0314861 A1 10/2016 Bernier et al.

OTHER PUBLICATIONS

Preliminary French Search Report for French Application No. FR 15 57264 dated Apr. 14, 2016.
Ruikar et al., "Extraction of Uranium, Plutonium and some Fission Products with Y-Irradiated Unsymmetrical and Branched Chain Dialkylamides" In: Journal of Radioanalytical and Nuclear Chemistry 1993, No. 176(2), pp. 103-111.
Prabhu et al., "Extraction of Uranium(VI) and Plutonium(IV) with Unsymmetrical Monoamides" In: Radiochimica Acta 1993, No. 60, pp. 109-114.
Cui et al., "Extraction of U(VI) with unsymmetrical N-methyl-N-decylalkylamide in toluene" In: Radiochimica Acta Jan. 4, 2005, No. 93, pp. 287-290.
Sun et al., Extraction of U(VI) with unsymmetrical N-methyl-N-octyl alkylamides in toliene: In: Journal of Radioanalytical and Nuclear Chemistry 2005, vol. 264, No. 3, pp. 711-713.
U.S. Appl. No. 15/747,713 entitled "Method for the Treatment of an Aqueous Nitric Solution Resulting From Dissolving Spent Nuclear Fuel, Said Method Being Performed in a Single Cycle and Without Requiring Any Operation Involving Reductive Stripping of Plutonium", filed Jan. 25, 2018.
English Translation of the Written Opinion of the International Search Authority for PCT/EP2016/068016.

* cited by examiner

DISSYMMETRIC N,N-DIALKYLAMIDES, THE SYNTHESIS THEREOF AND USES OF SAME

This is a National Stage application of PCT international application PCT/EP2016/068016, filed on Jul. 28, 2016 which claims the priority of French Patent Application No. 15 57264, filed Jul. 29, 2015, both of which are incorporated herein by reference in their entirety.

TECHNICAL FIELD

The invention relates to novel dissymmetric N,N-dialkylamides and to a method for synthesis thereof.

It also relates to the use of these N,N-dialkylamides as extractants, to extract uranium and/or plutonium from an acid aqueous solution and in particular from an aqueous solution resulting from the dissolution of a spent nuclear fuel in nitric acid.

It also relates to the use of these N,N-dialkylamides as extractants, to separate totally or partially uranium from plutonium from an acid aqueous solution and in particular from an aqueous solution resulting from the dissolution of a spent nuclear fuel in nitric acid.

It further relates to a method for processing an aqueous solution resulting from the dissolution of a spent nuclear fuel in nitric acid, allowing the uranium and plutonium contained in the solution to be extracted, separated and decontaminated in a single cycle without having recourse to any plutonium reduction operation, and wherein one of these N,N-dialkylamides or a mixture of same is used as extractant.

The invention finds particular application in the processing of spent nuclear fuels comprising uranium (notably of oxides of uranium—UOX), or uranium and plutonium (notably of mixed oxides of uranium and plutonium—MOX).

STATE OF THE PRIOR ART

The PUREX process, that is implemented in all spent nuclear fuel processing plants existing throughout the world (La Hague in France, Rokkasho in Japan, Sellafield in the United Kingdom, etc), uses tri-n-butyl phosphate (or TBP) as extractant to recover uranium and plutonium via liquid-liquid extraction from aqueous solutions resulting from the dissolution of these fuels in nitric acid.

In this process, TBP is used in 30% (v/v) solution in an organic diluent (hydrogenated tetrapropylene (or TPH) or n-dodecane). This organic solution is commonly called a «solvent» in the field under consideration.

The recovery of uranium and plutonium with the PUREX process is conducted in several cycles:

a first purification cycle of uranium and plutonium (called «1CUPu»), intended to decontaminate the uranium and plutonium with respect to americium, curium and fission products, with a partitioning of uranium and plutonium into two aqueous streams in this first cycle via a reductive stripping of plutonium;
 a second purification cycle of uranium (called «2CU»), intended to complete uranium decontamination to reach the specifications laid down by ASTM standards for the end uranium product; and
 a second and, in some plants, a third purification cycle of plutonium (respectively called «2CPu» and «3CPu»), intended to complete plutonium decontamination to reach the specifications laid down by ASTM standards for the end plutonium product and for concentration thereof before conversion to oxide.

The performance levels of the PUREX process are satisfactory and the feedback of experience acquired since the start-up of plants using this process is positive.

However, the use of TBP has limits impeding the possibility with this extractant of reaching the objectives of simplicity, compactness and improved safety that have been set for future spent nuclear fuel processing plants which particularly target the partitioning of uranium and plutonium into two aqueous streams without the use of reducing agents.

These limits are the following:

the decontamination factors of uranium and plutonium with respect to some fission products (technetium and ruthenium) and transuranium elements (Np) are insufficient at the end of the first purification cycle, hence the impossibility of achieving with TBP a scheme which would lead to end products meeting the aforementioned specifications in a single cycle;
 the partitioning of uranium and plutonium into two aqueous streams requires the reducing of plutonium(IV) to plutonium(III) (since with TBP, the separation factor between uranium(VI) and plutonium(IV) is insufficient, irrespective of the acidity of the aqueous solution used to obtain such a separation), and as a result requires the use of high amounts of reducing and anti-nitrous agents which generate unstable and reactive species via degradation that are therefore restricting in terms of safety;
 TBP degradation products have an impact on the performance levels of the process; in particular, di-n-butyl phosphate (or DBP) leads to the formation of metal complexes of which some are insoluble and may cause retaining of plutonium in the solvent, hence the need to carry out an operation known as «Pu barrier», which is downstream of the plutonium reductive stripping and which is intended to complete this stripping;
 the risk of formation of a $3^{rd}$ phase induced by the presence of plutonium limits the implementation of a plutonium concentrating scheme (for risks of criticality) or of a scheme allowing the processing of spent nuclear fuels with high plutonium content such as MOX fuels issued from light water reactors or fast neutron reactors;
 the stripping of uranium from the solvent in which it was previously extracted is incomplete if conducted at ambient temperature, hence the need to perform this stripping at a temperature of 50° C. (which corresponds to the maximum temperature allowed by the flash point of the solvent); however, even at this temperature, the stripping of uranium is diluting (the organic/aqueous flow ratio (O/A) being lower than 1);
 the solubility of TBP, that is non-negligible in an aqueous phase (up to 300 mg/L depending on the acidity of the aqueous phase) necessitates washes with organic diluent of the aqueous phases resulting from the difference extraction cycles to recover the TBP solubilised in these aqueous phases; and
 the incineration of the spent TBP and the degradation products thereof generates secondary wastes including solid phosphate residues.

Therefore, with the prospect of future spent nuclear fuel processing plants that are simpler and more compact than current plants and having further improved safety, the Inventors have set out to develop a method which, whilst performing as well as the PUREX process in terms of the recovery and decontamination of uranium and plutonium contained in aqueous nitric solutions resulting from the dissolution of spent nuclear fuels, allows overcoming all the limits related to the use of TBP as extractant, and which in particular only comprises a single processing cycle and is free of any operation for reductive plutonium stripping.

The Inventors therefore first focused on finding extractants having the required properties allowing the possible development of such a method.

N,N-dialkylamides happen to represent a family of extractants that has been largely researched as an alternative to TBP for the processing of spent nuclear fuels, in particular because they generally have good affinity for uranium and plutonium under high acidity, are less soluble than TBP in an aqueous phase, are fully incinerable (CHON principle) and have degradation products that are less problematic than those of TBP.

There are two types of N,N-dialkylamides:
so-called «symmetric» N,N-dialkylamides since the two alkyl groups carried by the nitrogen atom are identical; and
so-called «dissymmetric» N,N-dialkylamides since the two alkyl groups carried by the nitrogen atom are different.

Symmetric N,N-dialkylamides were the first to be researched. For example, three French patent applications (FR-A-2 591 213, FR-A-2 642 561 and FR-A-2 642 562, hereafter references [1], [2] and [3]) relating to the use of symmetric N,N-dialkylamides as extractants for the processing of spent nuclear fuels, were filed in the 1980s of which two, namely references [1] and [3], envisage the possibility of partitioning uranium and plutonium with these N,N-dialkylamides without carrying out a reductive stripping of plutonium.

Some of the symmetric N,N-dialkylamides proposed in references [1] and [3] effectively allow co-extracting uranium(VI) and plutonium(IV) from a highly acidic aqueous solution, followed by separating thereof under lower acidity without having to reduce the plutonium.

However, these N,N-dialkylamides prove to afford lesser extraction of plutonium from a highly acidic aqueous phase than TBP. As a result, to obtain a quantitative extraction of plutonium, the number of extraction stages must be increased compared with the number required for TBP, which goes against the targeted objective of compactness.

Dissymmetric N,N-dialkylamides later became the subject of a certain number of studies among which mention can be made of those conducted by the Bhabha Atomic Research Centre in Bombay (see, for example, the publications by Ruikar et al., *Journal of Radioanalytical and Nuclear Chemistry* 1993, 176(2), 103-111, and by Prabhu et al., *Radiochimica Acta* 1993, 60, 109-114, hereafter references [4] and[5]), and those conducted by the group directed by Guo-Xin Sun at Jinan University (see, for example, the publications by Cui et al., *Radiochimica Acta* 2005, 93, 287-290, and by Sun et al., *Journal of Radioanalytical and Nuclear Chemistry* 2005, 264(3), 711-713, hereafter references [6] and [7]).

However, aside from the fact that the results of these studies are fragmentary and sometimes contradictory, none thereof suggest the possibility of separating uranium from plutonium without reducing the latter.

SUMMARY OF THE INVENTION

The invention therefore first proposes novel N,N-dialkylamides that are dissymmetric and meet the following formula (I):

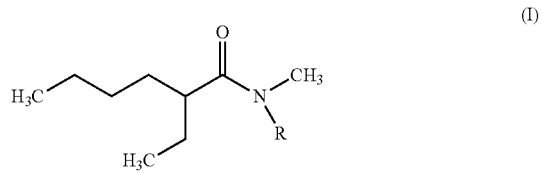

where R is a linear or branched alkyl group having from 8 to 15 carbon atoms.

In the foregoing and in the remainder hereof, the expressions «from . . . to . . . », «ranging from . . . to . . . » and «of between . . . and . . . » are equivalent and are meant to indicate that the limits are included.

Therefore:
by «linear alkyl group having from 8 to 15 carbon atoms» is meant any alkyl group selected from among n-octyl, n-nonyl, n-decyl, n-undecyl, n-dodecyl, n-tridecyl, n-tetradecyl and n-pentadecyl groups, whilst
by «branched alkyl group having from 8 to 15 carbon atoms» is meant any alkyl group comprising 8, 9, 10, 11, 12, 13, 14 or 15 carbon atom and having one or more branches, the same or different, such as n-heptyl, n-octyl, n-nonyl, n-decyl, n-undecyl, n-dodecyl, n-tridecyl or n-tetradecyl groups substituted by a methyl group (e.g. a 2-or 4-methylheptyl group, 2- or 4-methyloctyl group, 2- or 4-methyloctyl group, etc.); an n-hexyl, n-heptyl, n-octyl, n-nonyl, n-decyl, n-undecyl, n-dodecyl or n-tridecyl group substituted by an ethyl group (e.g. a 2- or 4-ethylhexyl group, 2- or 4-ethyloctyl group, 2- or 4-ethyldecyl group, etc); an n-octyl, n-nonyl, n-decyl, n-undecyl or n-dodecyl group substituted by an n-propyl or isopropyl group; an n-nonyl, n-decyl or n-undecyl group substituted by an n-butyl, isobutyl, sec-butyl or Cert-butyl group; an n-hexyl, n-heptyl, n-octyl, n-nonyl, n-decyl, n-undecyl, n-dodecyl or n-tridecyl group substituted by two methyl groups; an n-hexyl, n-heptyl, n-octyl, n-nonyl, n-decyl, n-undecyl or n-dodecyl group substituted by a methyl group and by an ethyl group (e.g. a 3-ethyl-4-methylhexyl group, 3-methyl-4-ethylhexyl group, 3-ethyl-4-methyloctyl group, 3-methyl-4-ethyloctyl group); etc.

Also, the expressions «aqueous solution» and «aqueous phase» are equivalent and interchangeable, and similarly the expressions «organic solution» and «organic phase» are equivalent and interchangeable.

According to the invention, it is preferred that the linear or branched alkyl group represented by R in foregoing formula (I) does not comprise more than 12 carbon atoms for reasons of viscosity (the viscosity of N,N-dialkylamides effectively being increased with the number of carbon atoms represented by R).

It is further preferred that this group should be selected from among the n-octyl, n-decyl, n-dodecyl, 2-ethylhexyl and 2-ethyloctyl groups, the n-octyl group being particularly preferred.

The above-defined N,N-dialkylamides are advantageously obtained by reacting a halide of following formula (II):

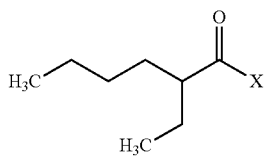

(II)

where X is a halogen atom and preferably a chlorine atom, with an amine of formula HN(CH$_3$)R where R is a linear or branched alkyl group having from 8 to 15 carbon atoms, in the presence of a base.

Therefore, a further subject of the invention is a method to synthesize N,N-dialkylamides, which comprises this reaction.

Said reaction can be performed either in an aqueous solution, in which case the base is sodium hydroxide or potassium hydroxide for example, or in an organic solvent such as dichloromethane or diethyl ether, in which case the base is triethylamine or diisopropylethylamine for example.

The N,N-dialkylamides defined in the foregoing have proved to be capable of extracting uranium(VI) and plutonium(IV) very efficiently from an acid aqueous solution such as a nitric aqueous solution.

A further subject of the invention is therefore the use of an N,N-dialkyl-amide or mixture of N,N-dialkylamides such as previously defined to extract uranium(VI) and/or plutonium(IV) from an acid aqueous solution.

According to the invention, the uranium and/or plutonium are preferably extracted from the acid aqueous solution by liquid-liquid extraction, i.e. by contacting this aqueous solution with an organic solution comprising the N,N-dialkylamide or mixture of N,N-dialkylamides in an organic diluent, followed by separating the aqueous and organic solutions.

In this case, the organic solution preferably comprises from 1 mol/L to 2 mol/L and better still from 1.3 mol/L to 1.5 mol/L of the N,N-dialkylamide or mixture of N,N-dialkylamides.

The acid aqueous solution is preferably an aqueous solution resulting from the dissolution of a spent nuclear fuel in nitric acid, i.e. an aqueous solution typically comprising from 3 mol/L to 6 mol/L of nitric acid.

In addition to being capable of quantitatively extracting uranium(VI) and plutonium(IV) from an acid aqueous solution, the above-defined N,N-dialkylamides have proved to allow a subsequent separation of the uranium and plutonium thus extracted without reducing the plutonium, this separation possibly being:

either a total separation of the uranium and plutonium, i.e. whereby two aqueous solutions are obtained one comprising plutonium without uranium, and the other comprising uranium without plutonium;

or a partial separation of the uranium and plutonium, i.e. whereby two aqueous solutions are obtained one comprising a mixture of plutonium and uranium, and the other comprising uranium without plutonium.

Therefore, a further subject of the invention is the use of an N,N-dialkylamide or mixture of N,N-dialkylamides such as previously defined for a total or partial separation of uranium(VI) and plutonium(IV) from an acid aqueous solution, which use comprises:

a) a co-extraction of uranium and plutonium from the aqueous solution, this co-extraction comprising at least one contacting of the aqueous solution with an organic solution comprising the N,N-dialkylamide or mixture of N,N-dialkylamides as extractant in solution in an organic diluent, followed by a separation of the aqueous and organic solutions;

b) a stripping of the plutonium, in oxidation state +IV, from the organic solution resulting from step a), this stripping comprising at least one contacting of the organic solution with an aqueous solution comprising from 0.1 mol/L to 0.5 mol/L of nitric acid, followed by a separation of the organic and aqueous solutions; and c) an extraction of all or part of the uranium fraction contained in the aqueous solution resulting from step b), this extraction comprising at least one contacting of the aqueous solution with an organic solution identical to the organic solution used at step a), followed by a separation of the aqueous and organic solutions; whereby there are obtained an aqueous solution comprising either plutonium without uranium, or a mixture of plutonium and uranium, and an organic solution comprising uranium without plutonium.

The organic solution used at step a) and hence the one used at step c) preferably comprise from 1 mol/L to 2 mol/L and better still from 1.3 mol/L to 1.5 mol/L of the N,N-dialkylamide or mixture of N,N-dialkylamides.

Regarding the acid aqueous solution from which the uranium and plutonium are co-extracted, this is preferably an aqueous solution resulting from the dissolution of a spent nuclear fuel in nitric acid, i.e. an aqueous solution typically comprising from 3 mol/L to 6 mol/L of nitric acid.

The uranium contained in the organic solution resulting from step c) can be stripped from this phase by contacting the organic solution with an aqueous solution comprising no more than 0.05 mol/L of nitric acid, followed by a separation of the organic and aqueous solutions.

In addition to exhibiting the aforementioned properties, the above-defined N,N-dialkylamides have proved to allow an extraction of uranium(VI) and plutonium(IV) from an aqueous solution resulting from the dissolution of a spent nuclear fuel in nitric acid, with very high separation factors with respect to the main fission products contained in this solution.

Having regard to this accumulation of properties, these N,N-dialkyl-amides have allowed the development of a method for processing an aqueous nitric solution resulting from the dissolution of a spent nuclear fuel which, whilst performing as well as the PUREX process in terms of recovery and decontamination of the uranium and plutonium contained in such a solution, is free of any reductive stripping operation of plutonium and only comprises a single processing cycle.

Therefore, a further subject of the invention is a single-cycle method for processing an aqueous solution resulting from the dissolution of a spent nuclear fuel in nitric acid, the aqueous solution comprising uranium plutonium, americium, curium and fission products including technetium, the cycle comprising:

a) a co-extraction of uranium and plutonium from the aqueous solution, the co-extraction comprising at least one contacting, in an extractor, of the aqueous solution with an organic solution comprising an N,N-dialkylamide or mixture of N,N-dialkylamides as above defined as extractant, in solution in an organic diluent, followed by a separation of the aqueous and organic solutions;

b) a decontamination of the organic solution resulting from step a) with respect to americium, curium and fission products, this decontamination comprising at least one contacting, in an extractor, of the organic solution with an aqueous solution comprising from 0.5 mol/L to 6 mol/L of nitric acid, followed by a separation of the organic and aqueous solutions;

c) a partitioning of the uranium and plutonium contained in the organic solution resulting from step b) into an aqueous solution comprising either plutonium without uranium, or a mixture of plutonium and uranium, and an organic solution comprising uranium without plutonium, this partitioning comprising:

$c_1$) a stripping of plutonium, in oxidation state +IV, and of a fraction of uranium from the organic solution resulting from step b), this stripping comprising at least one contacting, in an extractor, of the organic solution with an aqueous solution comprising from 0.1 mol/L to 0.5 mol/L of nitric acid, followed by a separation of the organic and aqueous solutions;

$c_2$) an extraction of all or part of the uranium fraction contained in the aqueous solution resulting from step $c_1$), this extraction comprising at least one contacting, in an extractor, of the aqueous solution with an organic solution identical to the organic solution used at step a), followed by a separation of the aqueous and organic solutions;

d) a decontamination of the organic solution resulting from step $c_1$) with respect to technetium, the decontamination comprising:

$d_1$) a stripping of technetium, in oxidation state +IV, from the organic solution resulting from step $c_1$), this stripping comprising at least one contacting, in an extractor, of the organic solution with an aqueous solution comprising from 0.1 mol/L to 3 mol/L of nitric acid and at least one reducing agent capable of reducing technetium from oxidation state +VII to oxidation state +IV, followed by a separation of the organic and aqueous solutions;

$d_2$) an extraction of the uranium fraction contained in the aqueous solution resulting from step $d_1$), this extraction comprising at least one contacting, in an extractor, of the aqueous solution with an organic solution identical to the organic solution used at step a), followed by a separation of the aqueous and organic solutions;

e) a stripping of uranium from the organic solution resulting from step $d_1$), this stripping comprising at least one contacting, in an extractor, of the organic solution with an aqueous solution comprising no more than 0.05 mol/L of nitric acid, followed by a separation of the organic and aqueous solutions; and f) a regeneration of the organic phase resulting from step e); whereby a first and second aqueous solution are obtained, decontaminated with respect to americium, curium and fission products including technetium, the first aqueous solution comprising either plutonium without uranium, or a mixture of plutonium and uranium, and the second aqueous solution comprising uranium without plutonium.

According to the invention, the organic solution used at step a) and hence those used at steps $c_2$) and $d_2$), since the organic solutions used at steps a), $c_2$) and $d_2$) have the same composition, preferably comprise from 1 mol/L to 2 mol/L and better still from 1.3 mol/L to 1.5 mol/L of the N,N-dialkylamide or mixture of N,N-dialkylamides.

As previously indicated, the aqueous solution used at step b) may comprise from 0.5 mol/L to 6 mol/L of nitric acid.

However, it is preferred that this aqueous solution comprises from 4 mol/L to 6 mol/L of nitric acid to facilitate the stripping of ruthenium and technetium from the organic solution resulting from step a). In this case, step b) advantageously also comprises a de-acidification of the organic solution, this de-acidification comprising at least one contacting of the organic solution with an aqueous solution comprising from 0.1 mol/L to 1 mol/L and better still 0.5 mol/L of nitric acid, followed by a separation of the organic and aqueous solutions.

According to the invention, the contacting of the organic and aqueous solutions in the extractor in which step $c_1$) takes place, comprises the circulation of these solutions in an O/A flow ratio that is advantageously higher than 1, preferably 3 or higher and better still 5 or higher, so as to obtain a concentrating stripping of plutonium, i.e. a plutonium stripping which leads to an aqueous solution in which the concentration of plutonium is greater than the concentration of this element in the organic solution from which it is stripped.

The reducing agent(s) in the aqueous solution used at step $d_1$) are preferably selected from among uranous nitrate (also called «U(IV)»), hydrazinium nitrate (also called «hydrazine nitrate»), hydroxylammonium nitrate (also called «hydroxylamine nitrate»), acetaldoxime and mixtures thereof such as a mixture of uranous nitrate and hydrazinium nitrate, a mixture of uranous nitrate and hydroxylammonium nitrate or a mixture of uranous nitrate and acetaldoxime, preference being given to a mixture of uranous nitrate and hydrazinium nitrate or a mixture of uranous nitrate and hydroxylammonium nitrate that are preferably used in a concentration ranging from 0.1 mol/L to 0.3 mol/L and typically of 0.2 mol/L.

In addition, step $d_1$), that can be conducted at ambient temperature, is preferably conducted however at a temperature ranging from 30 to 40° C. and better still at 32° C. to promote the stripping kinetics of technetium whilst best limiting phenomena of re-oxidization of this element in aqueous phase. The extractor in which step $d_1$) takes place is therefore preferably heated to a temperature of between 30° C. and 40° C.

According to the invention, preferably step $d_2$) additionally comprises an acidification of the aqueous solution resulting from step $d_1$), this acidification comprising the addition of nitric acid to the extractor in which step $d_2$) takes place to bring the concentration of nitric acid in the aqueous solution to a value of at least 2.5 mol/L.

Step e) can be conducted at ambient temperature. However, it is preferably conducted at a temperature ranging from 40° C. to 50° C., here also to promote the stripping of uranium. The extractor in which step e) takes place is therefore preferably heated to a temperature of between 40° C. and 50° C.

Irrespective of the temperature at which step e) is conducted, the contacting of the organic and aqueous solutions in the extractor in which this step takes place comprises the circulation of these solutions with an O/A flow ratio higher than 1 so as to obtain a concentrating stripping of uranium, i.e. a uranium stripping leading to an aqueous solution in which the concentration of uranium is higher than the concentration of this element in the organic solution from which it is stripped.

As previously indicated, the method of the invention further comprises a step f) to regenerate the organic solution resulting from step e), this regeneration preferably comprising at least one washing of the organic solution with a basic aqueous solution, followed by at least one washing of the organic solution with an aqueous solution of nitric acid.

The method of the invention, in addition to those already mentioned, has the following advantages:

the stripping of uranium is easier to implement than with the PUREX process since it can be performed both at ambient temperature and under heat, and using an O/A flow ratio higher than 1, thereby allowing a concentrating stripping of uranium which is not possible with the PUREX process;

through the fact that it does not involve any plutonium reduction reaction and thereby eliminates any risk of plutonium re-oxidization, the plutonium stripping is also easier to implement than with the PUREX process and can be performed in more concentrating manner than in this latter process; the importance of these advantages is all the greater since future spent nuclear fuel processing plants will have to process fuels with higher plutonium content (such as MOX fuels from light water or fast neutron reactors) than the fuels currently being reprocessed;

the degradation products (via hydrolysis and radiolysis) of the N,N-dialkylamides are less problematic than those of TBP because they are water-soluble and do not form complexes likely to retain plutonium;

the N,N-dialkylamides typically have a solubility in an aqueous phase 100 to 200 times lower than that of TBP, and it can thus be envisaged to omit or at least reduce the number of washes in organic diluent of the aqueous solutions resulting from the method of the invention, compared with the number provided in the PUREX process;

since the N,N-dialkylamides and the degradation products thereof only comprise carbon, hydrogen, oxygen and nitrogen atoms, they are fully incinerable and therefore do not produce penalising secondary wastes, contrary to TBP and its degradation products.

Other characteristics and advantages of the invention will become apparent from the following additional description referring to the appended Figures.

However, this additional description is only given to illustrate the subject-matter of the invention and is not under any circumstances to be construed as limiting this subject-matter.

DETAILED DESCRIPTION OF PARTICULAR EMBODIMENTS

I—Synthesis of N,N-Dialkylamides of the Invention

Figure 1:
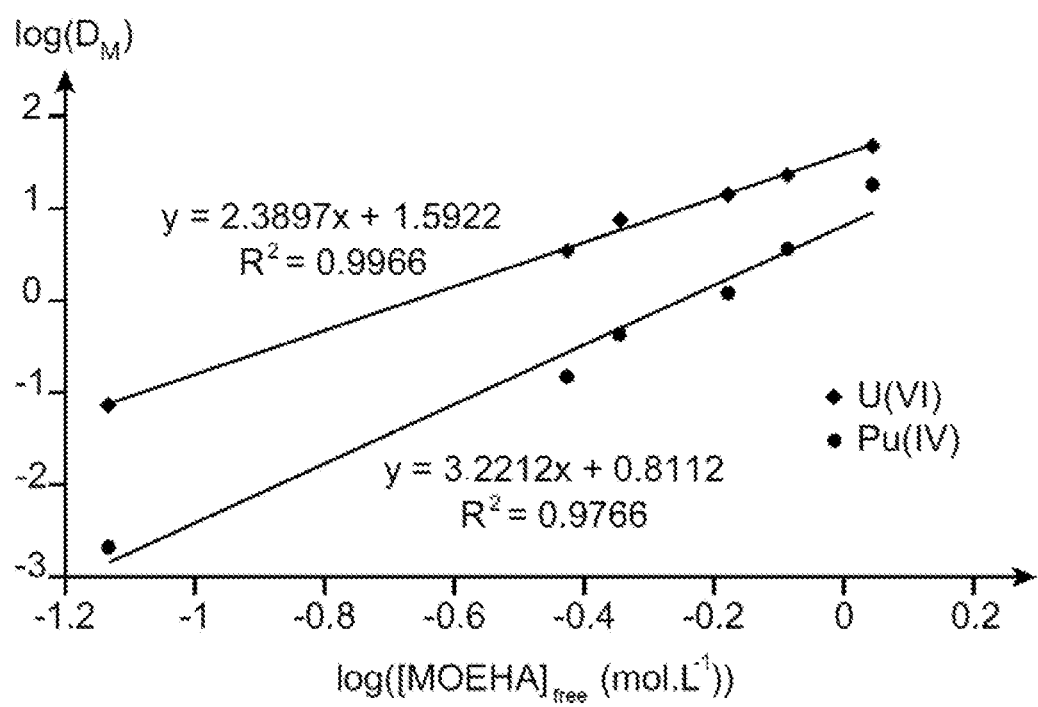
FIG. 1 illustrates by two straight lines the variation in the logarithm of the distribution coefficients, denoted $D_M$, of uranium and of plutonium such as obtained with extraction tests conducted with an N,N-dialkylamide of the invention, as a function of the logarithm of the free concentration (in mol/L) of this free N,N-dialkylamide in the organic phase used in these extraction tests.

As previously mentioned, the N,N-dialkylamides of the invention can be obtained with the following reaction scheme A:

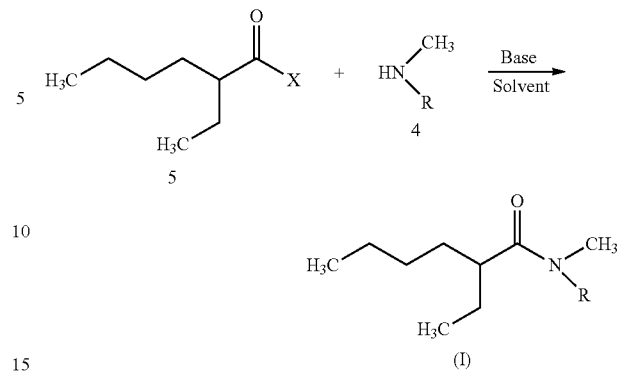

where X=halogen atom and R=linear or branched $C_8$ to $C_{15}$ alkyl group.

When the amine denoted 4 in the above scheme is not commercially available, it can be obtained with the following reaction scheme B:

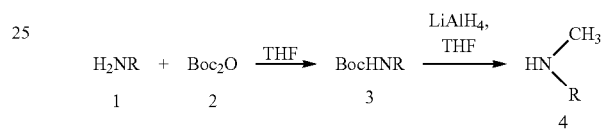

where R=linear or branched $C_8$ to $C_{15}$ alkyl group.

I.1—Synthesis of N-methyl-N-octyl-2-ethylhexanamide or MOEHA

MOEHA, which meets the above formula (I) where R is an n-octyl group, is synthesized from 2-ethylhexanoyl chloride and N-methyl-N-octylamine, in the presence of sodium hydroxide in water (reaction scheme A).

For this purpose, sodium hydroxide (30% NaOH-112 g-0.839 mole-1.19 eq.), water (100 g) and N-methyl-N-octylamine (100 g-0.698 mole-1 eq.) are placed in a fully equipped 500 mL reactor. The system is placed under agitation, the set temperature is 4° C. The 2-ethylhexanoyl chloride (136.5 g-0.839 mole-1.19 eq.) is poured at a bulk temperature of between 14° C. and 17° C. (pour time: 90 minutes). The progress of the reaction is controlled and shows the presence of 0.6% of residual amine. The formation is obtained of 90% of MOEHA and 8.8% of an unknown impurity. The medium is heated to 50° C. for 30 minutes to consume the residual amine. The medium is then cooled to 20° C. and decanted. The organic phase is washed twice with 100 mL water to obtain 208 g of reaction product.

The MOEHA is subsequently obtained with 98.3% purity (measured by gas phase chromatography coupled to a flame ionization detector—or GC-FID) after two distillations under pressure (of 2 and 8 mbar respectively).

$^{13}$C NMR (100 MHz, CDCl$_3$, 25° C.) δ (ppm): 3.37 (t, J=7.0, 2H, 2H$_{\alpha A}$); 3.28 (t, J=7.0, 2H, 2H$_{\alpha B}$); 3.00 (s, 3H, CH$_{3A}$); 2.92 (s, 3H, CH$_{3B}$); 2.61 -2.42 (m, 2H, H$_{2A}$et H$_{2B}$); 1.90-1.77 (m, 2H, CH$_{2A}$); 1.71-1.35 (m, 10H, 2CH$_{2A}$ and 3CH$_{2B}$); 1.34- 1.11 (m, 28H, 7CH$_{2A}$ and 7CH$_{2B}$); 0.94-0.77 (m, 18H, 3CH$_{3A}$ and CH$_{3B}$)

$^1$H NMR (400 MHz, CDCl$_3$, 25° C.) δ (ppm): 176.2; 176.0 (CO$_A$ and CO$_B$); 50.1; 48.1 (C$_{\alpha A}$ and C$_{\alpha B}$); 43.2; 42.9 (C$_{2A}$ and C$_{2B}$); 35.6; 33.8 (CH$_{3A}$ and CH$_{3B}$); 32.8; 32.7; 31.9; 31.9; 30.1; 30.0; 29.5; 29.4; 29.4; 29.3; 29.2; 27.5;

27.5; 27.0; 26.9; 26.2; 23.1; 23.0; 22.8 (20CH$_2$); 14.2; 14.2; 14.1; 14.1 (2CH$_{3A}$ and 2CH$_{3B}$); 12.3; 12.2 (CH$_{3A}$ and CH$_{3B}$)

MS (EI), m/z (I %): 269 (5%) [M]+, 240 (22%) [M-C$_2$H$_5$]+, 226 (22%) [M-C$_3$H$_7$]+, 212 (40%) [M-C$_4$H$_9$]+, 198 (25%) [M-C$_5$H$_{11}$]+, 170 (100%) [M -C$_7$H$_{15}$]+, 142 (5%) [C$_9$H$_{20}$N]+, 127 (5%) [C$_8$H$_{15}$O]+

HRMS (EI): m/z calculated for [MH]+(C$_{17}$H$_{35}$NO) 269.2714; found 269.2672

I.2—Synthesis of N-decyl-N-methyl-2-ethylhexanamide or MDEHA

MDEHA, which meets above formula (I) where R is an n-decyl group, is synthesized following reaction scheme A from 2-ethylhexanoyl chloride and N-decyl-N-methylamine, in the presence of triethylamine (Et$_3$N) in anhydrous dichloromethane (DCM) (reaction scheme A).

For this purpose, the dichloromethane (100 mL), Et$_3$N (21.2 g-0.21 mole-1.48 eq.) and N-decyl-N-methylamine (24 g-0.14 mole-1 eq.) are placed in a fully equipped 500 mL reactor. The system is placed under agitation and cooled to 0° C. The 2-ethylhexanoyl chloride (25 g-0.15 mole-1.1 eq.) is then poured at a bulk temperature of between 5° C. and 16° C. (pour time: 45 minutes). Under agitation, the bulk temperature gradually rises to ambient temperature. After 90 minutes, the progress of the reaction is controlled and shows that there no longer remains any initial amine but that there remains 5% of 2-ethylhexanoyl chloride. There is formation of 88.9% of MDEHA and 4.6% of an unknown impurity. The medium is then successively washed with twice 100 mL of a 10% sodium hydroxide solution, then twice with 100 mL of a 1 N hydrochloric acid solution and with 100 mL of a 5% sodium carbonate solution. The organic phase is concentrated under reduced pressure to obtain 43.6 g of an oil. This oil contains 89% of MDEHA and 9.46% of the unknown impurity.

The MDEHA is subsequently obtained with 99.4% purity (measured by GC-FID) after two distillations under pressure (1.5 mbar).

MS (EI), m/z (I %): 297 (3%) [M]+, 268 (13%) [M-C$_2$H$_5$]+, 254 (15%) [M-C$_3$H$_7$]+, 240(12%) [M-C$_4$H$_9$]+, 226 (12%) [M-C$_5$H$_{11}$]+, 198 (100%) [M-C$_7$H$_{15}$]+

HRMS (EI): m/z calculated for [M]+(C$_{19}$H$_{39}$NO) 297.3026; found 297.3000.

I.3—Synthesis of N-dodecyl-N-methyl-2-ethylhexanamide or MDdEHA

MDdEHA, which meets above formula (I) where R is an n-dodecyl group, is synthesized from 2-ethylhexanoyl chloride and N-dodecyl-N-methylamine, in the presence of Et$_3$N in anhydrous DCM (reaction scheme A).

For this purpose, the DCM (150 mL), Et$_3$N (22.7 g-0.223 mole-1.49 eq.) and N-dodecyl-N-methylamine (30 g-0.15 mole-1 eq.) are placed in a fully equipped 500 mL reactor. The system is placed under agitation and cooled to about 0° C. The 2-ethylhexanoyl chloride (26 g-0.16 mole-1.06 eq.) is then poured at a bulk temperature of between 0° C. and 2° C. (pour time: 40 minutes). Under agitation, the bulk temperature gradually rises to ambient temperature. After 4 hours, the progress of the reaction is controlled and shows that there no longer remains any starting amine. There is formation of 97% of MDdEHA. The medium is successively washed twice with 100 mL of a 10% sodium hydroxide solution and once with 100 mL of a 5% sodium carbonate solution. The organic phase is then concentrated under reduced pressure to obtain 55.5 g of an oil.

The MDdEHA is subsequently obtained with 99.5% purity (measured by GC-FID) after a single distillation under much reduced pressure (0.7 mbar).

MS (EI) m/z (I %): 325 (3%) [M]+, 296 (11%) [M-C$_2$H$_5$]+, 282 (12%) [M-C$_3$H$_7$]+, 268 (15%) [M-C$_4$H$_9$]+, 254 (10%) [M-C$_5$H$_{11}$]+, 226 (100%) [M-C$_7$H$_{15}$]+

HRMS (EI): m/z calculated for [M]+(C$_{21}$H$_{43}$NO) 325.3339; found 325.3325.

I.4—Synthesis of N-2-ethylhexyl-N-methyl-2-ethylhexanamide or M(2-EH)EHA

M(2-EH)EHA, which meets above formula (I) where R is a 2-ethylhexyl group, is synthesized from 2-ethylhexanoyl chloride and N-methyl-2-ethylhexanamine, in the presence of Et$_3$N in anhydrous DCM (reaction scheme A), the N-methyl-2-ethylhexanamine having been previously synthesized from 2-ethylhexylamine (reaction scheme B).

Synthesis of N-methyl-2-ethylhexanamine

To a solution of 2-ethylhexylamine (15.0 mL-90.5 mmol-1 eq.) in anhydrous tetrahydrofuran (THF) (70 mL) is added dropwise at 0° C., using an addition funnel, a solution of di-cert-butyl dicarbonate (Boc$_2$O-23.7 g-108.0 mmol-1.2 eq.) in anhydrous THF (30 mL). The mixture is left under agitation for 20 hours at ambient temperature and then concentrated under a controlled vacuum (0.150 mbar/20° C.). The crude oil obtained is purified by silica gel chromatography (elution: 100% DCM) and, after controlled vacuum concentration (0.035 mbar/40° C.), gives compound 3 of reaction scheme B where R is a 2-ethylhexyl group (21 g) in the form of a colourless oil.

To a solution of compound 3 (5.0 g-21.8 mmol-1 eq.) in anhydrous THF (100 mL) cooled to 0° C. is added dropwise over 10 minutes a solution of aluminium hydride and lithium (LiAlH$_4$) at 2.4 mol/L in THF (13.6 mL-32.7 mmol-1.5 eq.). The mixture is left to return to ambient temperature and then heated to 50° C. for 16 hours. After return to ambient temperature, the reaction mixture is carefully hydrolysed with successive dropwise additions of ethylacetate (1 mL), water (1.2 mL), 12 N sodium hydroxide (2.5 mL) then water (2.4 mL). After 20 minutes under strong agitation, the mixture is filtered on a Büchner. The filtrate is concentrated under a controlled vacuum (0.035 mbar, 15° C.) to give N-methyl-2-ethylhexanamine (3.0 g) in the form of a colourless oil. This oil is used at the following step without additional purification.

Synthesis of M(2-EH)EHA

To a solution of N-methyl-2-ethylhexanamine (3.0 g-20.9 mmol-1 eq.) in anhydrous DCM (40 mL), cooled to 0° C., are added dropwise Et$_3$N (4.4 mL; 31.4 mmol; 1.5 eq.), then 2-ethylhexanoyl chloride (3.6 mL-20.9 mmol-1 eq.). The mixture is left under agitation for 20 hours at ambient temperature after which water (40 mL) is added. The phases are decanted and the aqueous phase is extracted with DCM (2×40 mL). The organic phases are combined, dried over sodium sulfate, filtered and concentrated under reduced pressure. The crude oil obtained is purified by silica gel chromatography (elution: 100% DCM) to give a 98.5% pure fraction (HPLC at 210 nm) of M(2-EH)EHA (2.6 g) in the form of a pale yellow oil. With the recovered impure fractions, the yield of the synthesis from 2-ethylhexanamine is estimated to be 71%.

$^{13}$C NMR, DEPT (CDCl$_3$) δ(ppm): 176.6 (C=O), 53.8 (CH$_2$), 51.5 (CH$_2$), 43.1 (CH$_3$), 42.7 (CH$_3$), 38.9 (CH), 37.3 (CH), 36.1 (CH), 34.6 (CH), 32.5 (CH$_2$), 30.5(CH$_2$), 29.9 (CH$_2$), 28.7 (CH$_2$), 25.9(CH$_2$), 23.6(CH$_2$), 23.1(CH$_2$), 22.9 (CH$_2$), 14.0(CH$_3$), 12.1(CH$_3$), 10.8(CH$_3$), 10.5(CH$_3$).

$^{1}$H NMR (CDCl$_3$) δ(ppm): 3.16 (d, 2H, 1CH$_2$, rotamer 1), 3.30 (d, 2H, 1CH$_2$, rotamer 2), 2.90 (s, 3H, 1CH$_3$, rotamer 1), 2.98 (s, 3H, 1CH$_3$, rotamer 2), 2.54 (m, 1H, 1CH), 1.61 (m, 3H, 1CH$_2$+1CH), 1.42 (m, 2H,CH$_2$), 1.25 (m, 12H, 6CH$_2$), 0.84 (m, 12H, 4CH$_3$).

MS (ESI$^+$), m/z: 270.3 [MH]$^+$, 292.3 [MNa]$^+$

I.5—Synthesis of N-2-ethyloctyl-N-methyl-2-ethylhexanamide or M(2-EO)EHA

M(2-EO)EHA, which meets above formula (I) where R is a 2-ethyloctyl group, is synthesized from 2-ethylhexanoyl chloride and N-methyl-N-2-ethyloctanamine, in the presence of Et$_3$N in anhydrous DCM (reaction scheme A), the N-methyl-N-2-ethyloctanamine having been previously synthesized from 2-ethyloctylamine (reaction scheme B) which itself is obtained by coupling 1-bromohexane and butyronitrile, followed by reduction of the resulting 2-ethyloctanenitrile.

Synthesis of N-methyl-N-2-ethyloctanamine

To a solution of diisopropylamine (11.3 mL-80.0 mmol-1 eq.) in anhydrous THF (42 mL) cooled to −78° C., n-butyl-lithium is added (n-BuLi-2.5 M in hexanes; 32.0 mL-80.0 mmol-1 eq.). Agitation is maintained for 10 minutes at −78° C. after which the butyronitrile (7.0 mL-80.0 mmol-1 eq.) is added dropwise. Agitation is maintained for 10 minutes at −78° C. and 1-bromohexane (11.3 mL-80.0 mmol-1 eq.) is then added dropwise. The mixture is left under agitation for 20 hours with gradual return to ambient temperature. A saturated ammonium chloride solution is added (40 mL) followed by diethylether (Et$_2$O-50 mL). The phases are decanted and the aqueous phase is extracted with Et$_2$O (2×50 mL). The combined organic phases are dried over sodium sulfate, filtered and evaporated under controlled pressure (15° C./0.050 mbar). The crude oil obtained is purified by silica gel chromatography (elution: cyclohexane/DCM) to give 2-ethyloctane-nitrile (60 weight % solution of 24 g with DCM/cyclohexane, i.e. estimated 9.8 g) in the form of a pale yellow solution.

To a solution of 2-ethyloctanenitrile (7.18 g-45.6 mmol-1 eq.) in anhydrous THF (100 mL), cooled to 0° C., is added dropwise over 10 minutes a solution of LiAlH$_4$ (2.4 M in THF; 38.1 mL-91.3 mmol-2 eq.). The mixture is returned to ambient temperature then heated to 50° C. for 16 hours. After return to 0° C., the reaction mixture is carefully hydrolysed with successive dropwise additions of ethylacetate (3mL), water (3.3 mL), 12 N sodium hydroxide (7 mL) then water (6.7 mL). After 20 minutes under strong agitation, the mixture is filtered on a Büchner. The filtrate is concentrated under a controlled vacuum (0.150 mbar, 35° C.) to give 2-ethyloctylamine (7.0 g in 55 weight % solution in THF) in the form of a colourless oil. This oil is used at the following step without additional purification.

The synthesis of N-methyl-N-2-ethyloctanamine from the 2-ethyloctyl-amine thus obtained is performed by following a similar operating protocol to the one previously described for the synthesis of N-methyl-N-ethylhexanamine.

Synthesis of M(2-EO)EHA

To a solution of N-methyl-N-2-ethyloctanamine (5.6 g-33.0 mmol-1 eq.) in anhydrous DCM (60 mL), cooled to 0° C., are added dropwise Et$_3$N (6.8 mL-49.5 mmol-1.5 eq.) and then 2-ethylhexanoyl chloride (5.6 mL-33.0 mmol-1 eq.). The mixture is left under agitation for 20 hours at ambient temperature after which water (60 mL) is added. The phases are decanted and the aqueous phase is extracted with DCM (2×60 mL). The combined organic phases are dried over sodium sulfate, filtered and concentrated under reduced pressure. The crude oil obtained is purified by silica gel chromatography (elution: 100% DCM) to give a 98.3% pure fraction (HPLC at 210 nm) of M(2-EO)EHA (2.6 g) in the form of a pale yellow oil. With the recovered impure fractions, the yield of the step is estimated to be 64%.

$^{13}$C NMR, DEPT (CDCl$_3$) δ(ppm): 176.2 (C=O), 53.8 (CH$_2$), 51.5 (CH$_2$), 43.2 (CH$_3$), 42.7 (CH$_3$), 39.0 (CH), 37.3 (CH), 36.1 (CH), 34.7 (CH), 32.5 (CH$_2$), 31.8 (CH$_2$), 30.8 (CH$_2$), 29.8 (CH$_2$), 29.7 (CH$_2$), 26.5 (CH$_2$), 26.0 (CH$_2$), 23.7 (CH$_2$), 22.9 (CH$_2$), 22.6 (CH$_2$), 14.0(CH$_3$), 12.1(CH$_3$), 10.8(CH$_3$), 10.5(CH$_3$)

$^{1}$H NMR (CDCl$_3$) δ(ppm): 3.34 (m, 2H, 1CH$_2$, rotamer 1), 3.22 (m, 2H, 1CH$_2$, rotamer 2), 3.03 (s, 3H, 1CH$_3$, rotamer 1), 2.95 (s, 3H, 1CH$_3$, rotamer 2), 2.59 (m, 1H, 1CH), 1.65 (m, 3H, 1CH$_2$+1CH), 1.49 (m, 2H, 1CH$_2$), 1.29 (m, 16H, 8CH$_2$), 0.90 (m, 12H, 4CH$_3$)

MS (ESI$^+$), m/z: 298.4 [MH]$^+$, 320.4 [MNa]$^+$

II—Extracting Properties of the N,N-Dialkylamides if the Invention

II.1—Acquisition of the Distribution Coefficients of Uranium and Plutonium, and of the Separation Factors $FS_{U/Pu}$, from a Synthetic Aqueous Solution of Uranium and Plutonium, for MOEHA, MDEHA and MDdEHA First, extraction tests were carried out using:
as organic phases: solutions comprising 1.4 mol/L MOEHA, MDEHA or MDdEHA in TPH; and
as aqueous phases: aliquots of an aqueous solution comprising 90 g/L of uranium(VI), about 70 mg/L of plutonium(IV) and 4.15 mol/L of HNO$_3$.

Stripping tests were then conducted using:
as organic phases: the organic phases obtained after the foregoing extraction tests; and
as aqueous phases: aliquots of an aqueous solution comprising 0.1 mol/L of HNO$_3$.

Each of these tests was conducted by placing in contact an organic phase with an aliquot of aqueous solution, in a tube under agitation, for 15 minutes at 25° C. The O/A volume ratio used was 1 for the extraction tests and 1 for the stripping tests. These phases were separated from one another after centrifugation.

The concentrations of uranium and plutonium were measured in the separated organic and aqueous phases by X-ray fluorescence for uranium and by α-spectrometry for plutonium.

Table 1 below, for each tested N,N-dialkylamide, gives the concentrations of uranium denoted $[U]_{org}$, such as obtained in the organic phases after the extraction tests, the distribution coefficients of uranium denoted $D_U$, and of plutonium denoted $D_{Pu}$, such as obtained after the extraction and stripping tests, the concentrations of nitric acid denoted $[HNO_3]_{aq.}$, such as obtained in the aqueous phases after the extraction and stripping tests, and the U/Pu separation factors denoted $FS_{U/Pu}$, such as obtained after the stripping tests.

This Table also gives the experimental results obtained under the same operating conditions but using solutions comprising N,N-dialkylamides of the prior art as organic phases, namely:

a solution comprising 0.9 mol/L of N,N-di(2-ethylhexyl)-isobutanamide (or DEHiBA) and 0.5 mol/L of N,N-di(2-ethylhexyl)-n-butanamide (or DEHBA) in TPH, these two N,N-dialkylamides being proposed in reference [3] under the names DOiBA and DOBA; and a solution comprising 1.4 mol/L of N,N-di(2-ethylhexyl)-3,3-dimethylbutanamide (or DEHDMBA) in TPH, this N,N-dialkylamide being proposed in reference [1] under the name DOTA.

sion spectrometry (or ICP-AES) whilst the concentrations of uranium in the organic phases were determined by stripping these elements in water and measuring their concentration by ICP-AES in the aqueous phases resulting from this stripping. The plutonium concentrations were measured in the aqueous and organic phases by α-spectrometry.

The results are illustrated in FIG. 1 which, in the form of two straight lines, illustrates the variation in the logarithm of the distribution coefficients, denoted $D_M$, of uranium and of plutonium, as a function of the logarithm of the free concentration (in mol/L) of MOEHA in organic phase (total concentration of MOEHA corrected for the fraction of nitric acid extracted in organic phase).

This Figure shows that the slope of the straight line corresponding to the extraction of uranium(VI) is close to 2, confirming the formation of a $UO_2(NO_3)_2(MOEHA)_2$ complex which conforms to complexes conventionally observed with N,N-dialkylamides.

TABLE I

| | | Organic phase | | | | |
|---|---|---|---|---|---|---|
| | | MOEHA 1.4M/TPH | MDEHA 1.4M/TPH | MdDEHA 1.4M/TPH | DEHiBA + DEHBA 0.9M + 0.5M/TPH | DEHDMBA 1.4M/TPH |
| Extraction | $[U]_{org.}$ (g/L) | 68 | 69 | 69 | 77 | 65 |
| | $D_U$ | 4.1 | 2.4 | 3.7 | 4.0 | 4.4 |
| | $D_{Pu}$ | 2.2 | 1.8 | 1.7 | 0.74 | 1.0 |
| | $[HNO_3]_{aq.}$ (mol/L) | 4.16 | 4.17 | 4.17 | 4.14 | 4.14 |
| Stripping | $D_U$ | 0.81 | 0.83 | 0.82 | 0.63 | 0.61 |
| | $D_{Pu}$ | 0.046 | 0.056 | 0.058 | 0.057 | 0.033 |
| | $FS_{U/Pu}$ | 17.4 | 14.9 | 14.2 | 11.0 | 18.6 |
| | $[HNO_3]_{aq.}$ (mol/L) | 0.50 | 0.52 | 0.57 | 0.58 | 0.54 |

This Table shows that, under strong acidity, the N,N-dialkylamides of the invention extract uranium(VI) ($D_{U(VI)} \geq 2.4$) as well as the prior art N,N-dialkylamides, but they extract more strongly plutonium(IV) ($D_{Pu(IV)} \geq 1.7$) than the latter.

It also shows that plutonium(IV) can subsequently be easily stripped from the organic phase using an aqueous nitric solution of low acidity ($[HNO_3]=0.5$ M) whereas the uranium preferably remains held in this organic phase ($FS_{U/Pu} > 14$).

II-2—Study on the Stoichiometry of Complexes Formed by MOEHA with Uranium and Plutonium:

Extraction tests were conducted using:
as organic phases: solutions respectively comprising 0.1 mol/L, 0.5 mol/L, 0.75 mol/L, 1.0 mol/L, 1.25 mol/L, 1.5 mol/L and 2 mol/L of MOEHA in TPH; and
as aqueous phases: aliquots of an aqueous solution comprising 2 g/L of uranium(VI), 1 mol/L of $HNO_3$ and 2 mol/L of $LiNO_3$, and aliquots of an aqueous solution comprising $1.7 \times 10^{-4}$ mol/L of plutonium(IV), 1 mol/L of $HNO_3$ and 2 mol/L of $LiNO_3$.

For these tests, each organic phase was placed in contact with an aliquot of aqueous solution, in a tube under agitation, for 15 minutes at 25° C., with an O/A volume ratio of 1. These phases were then separated from one another after centrifugation.

The concentrations of uranium were measured in the aqueous phases by inductively coupled plasma atomic emis- On the other hand, according to these results, the complex formed by MOEHA with plutonium(IV) appears to involve three molecules of MOEHA per one $Pu^{4+}$ cation, thereby giving a Pu:MOEHA stoichiometry of 1:3 ($Pu(NO_3)_4(MOEHA)_3$), already observed with other dissymmetric N,N-dialkylamides (reference [5]). The extraction equilibrium of plutonium(IV) by MOEHA can therefore be written as follows:

$$Pu^{4+} + 4NO_3^- + 3\overline{MOEHA} \leftrightarrow \overline{Pu(NO_3)_4 MOEHA_3}$$

II.3—Acquisition of the Distribution Coefficients of Uranium, Plutonium and Fission Products, from an Aqueous Solution Resulting from the Dissolution of Nuclear Fuel Pellets in $HNO_3$, for MOEHA Extraction tests were performed using:
as organic phase: a solution comprising 1.4 mol/L of MOEHA in TPH; and
as aqueous phase: an aqueous solution previously obtained by dissolving pellets derived from different irradiated fuels of UOX-BWR type (Boiling Water Reactor) and UOX-PRW type (Pressurised Water Reactor) in 5 M nitric acid.

This aqueous solution comprises 4.3 mol/L of $HNO_3$ and its element composition is given in Table II below.

TABLE II

| Element | Concentration (g/L) | Element | Concentration (g/L) | Element | Activity (Bq/L) |
|---|---|---|---|---|---|
| U(VI) | 244 | Si | 0.175 | $^{106}$Ru | $1.1 \times 10^{11}$ |
| Pu(IV) | 2.53 | Ba | 0.570 | $^{134}$Cs | $2.4 \times 10^{11}$ |
| Tc | 0.275 | Al | 0.145 | $^{137}$Cs | $1.1 \times 10^{12}$ |
| Np | 0.214 | Ca | 0.130 | $^{144}$Ce | $9.7 \times 10^{10}$ |
| Zr | 1.08 | K | 0.070 | $^{154}$Eu | $3.6 \times 10^{10}$ |
| Ru | 0.510 | Mg | 0.090 | $^{155}$Eu | $2.2 \times 10^{10}$ |
| Mo | 0.106 | Na | 0.135 | $^{241}$Am | $6.6 \times 10^{10}$ |
| Pd | 0.345 | Sr | 0.210 | | |
| Fe | 0.285 | | | | |

The organic phase, previously equilibrated at 6 mol/L of HNO$_3$, was placed in contact with the aqueous phase, in a tube under agitation, for 15 minutes at 25° C., with an O/A volume ratio of 2.5.

These phases were then separated from one another after centrifugation.

The concentrations of uranium and plutonium, and the activities of the β-γ isotopes were measured in each of the organic and aqueous phases thus separated, via X-ray fluorescence for uranium and plutonium, and γ-spectrometry for the β-γ isotopes.

The concentrations of Tc, Np, Zr, Mo and Fe were only able to be measured in the aqueous phase by ICP-AES, and the concentrations of these elements in the organic phase were estimated by the difference between the initial concentrations of said elements in the aqueous phase and those measured at equilibrium after extraction.

The results obtained in terms of aqueous phase acidity denoted $[H^+]_{aq.}$, of uranium and plutonium concentrations in the aqueous and organic phases respectively denoted $[U]_{aq.}$, $[U]_{org.}$, $[Pu]_{aq.}$ and $[Pu]_{org.}$, and of distribution coefficients denoted D, are given in Table III below.

This Table also gives the experimental results obtained under the same operating conditions but using as organic phase a solution comprising 30% (v/v) TBP in TPH.

TABLE III

| | Organic phase | |
|---|---|---|
| | MOEHA 1.4M/TPH | TBP 30% (v/v)/TPH |
| $[H^+]_{aq.}$ (mol/L) | 5.75 | 5.9 |
| $[U]_{aq.}$ (g/L) | 25 | 18 |
| $[U]_{org.}$ (g/L) | 89 | 91 |
| $[Pu]_{aq.}$ (mg/L) | 340 | 250 |
| $[Pu]_{org.}$ (mg/L) | 91 | 960 |
| $D_U$ | 3.5 | 4.9 |
| $D_{Pu}$ | 2.7 | 3.8 |
| $D_{Tc}$ | 1.1 | 0.69 |
| $D_{Np}$ | 2.2 | 2.2 |
| $D_{Zr}$ | 0.03 | 0.10 |
| $D_{Mo}$ | <0.1 | |
| $D_{Fe}$ | <0.01 | |
| $D_{(106Ru)}$ | $8.5 \times 10^{-4}$ | $2.8 \times 10^{-4}$ |
| $D_{(134Cs)}$ | $5.8 \times 10^{-5}$ | $1.5 \times 10^{-5}$ |
| $D_{(137Cs)}$ | $7.5 \times 10^{-5}$ | $1.8 \times 10^{-5}$ |
| $D_{(154Eu)}$ | $8.6 \times 10^{-5}$ | $3.8 \times 10^{-4}$ |
| $D_{(241Am)}$ | $2.3 \times 10^{-4}$ | $1.5 \times 10^{-4}$ |

This Table shows that the use of MOEHA as extractant leads to high distribution coefficients (>>1) for uranium(VI) and plutonium(IV) at an acidity of 5.75 mol/L of HNO$_3$, despite the strong uranium saturation of the organic phase (89 g of uranium/L).

It also shows that the use of MOEHA as extractant also leads to high separation factors $FS_{U/PF}$ and $FS_{Pu/PF}$, in particular with respect to ruthenium 106, since these are always higher than 3 000. The separation factors $FS_{U/Am}$ and $FS_{Pu/Am}$ are also very high.

These results that are very close to those observed under identical conditions but using TBP as extractant, confirm that the N,N-dialkylamides of the invention allow the extraction of uranium and plutonium quantitatively and selectively with respect to americium, curium and the main fission products likely to be contained in an aqueous solution resulting from the dissolution of a spent nuclear fuel in nitric acid, whilst subsequently allowing the partitioning of uranium and plutonium into two aqueous streams, the first comprising uranium without plutonium, and the second containing plutonium with or without uranium, without having to reduce the plutonium which is not the case with TBP.

II.4—Acquisition of the Distribution Coefficients of Uranium and Plutonium, and of the Separation Factors $FS_{U/Pu}$, from a Synthetic Aqueous Solution of Uranium and Plutonium, for M(2-EH)EHA and M(2-EO)EHA Extraction tests were conducted using:
- as organic phases: solutions comprising 0.5 mol/L of M(2-EH)EHA or M(2-EO)EHA in TPH; and
- as aqueous phases: aliquots of aqueous solutions of uranium(VI) (≈11.5 g/L) doped with plutonium(IV) (≈0.4 MBq/mL) and comprising either 4 mol/L of HNO$_3$ or 0.5 mol/L of HNO$_3$ (to simulate the aqueous phase of low acidity that is typically used to strip plutonium at a U/Pu partitioning step into two aqueous streams).

Each of these tests was performed by placing in contact an organic phase, in a tube under agitation, with an aliquot of aqueous solution for 15 minutes at 25° C. The O/A volume ratio used was 1. These phases were then separated from one another after centrifugation.

The concentration of uranium and the activity of plutonium ($^{239+240}$Pu) were measured in the organic and aqueous phases thus separated, using ICP-AES and α-spectrometry respectively.

Table IV below, for each tested N,N-dialkylamide, gives the distribution coefficients of uranium denoted $D_U$, and of plutonium denoted $D_{Pu}$, such as obtained, and the U/Pu separation factors, denoted $FS_{U/Pu}$, such as obtained with an acidity of 0.5 mol of HNO$_3$/L.

This Table also gives the experimental results obtained under the same operating conditions but using, as organic phases, aliquots of a solution comprising 0.5 mol/L of MOEHA in TPH.

TABLE IV

| | | Organic phase | | |
|---|---|---|---|---|
| | | M(2-EH)EHA 0.5M/TPH | M(2-EO)EHA 0.5M/TPH | MOEHA 0.5M/TPH |
| [HNO$_3$] 4M | $D_U$ | 0.95 | 0.98 | 1.64 |
| | $D_{Pu}$ | 0.056 | 0.049 | 0.185 |
| [HNO$_3$] 0.5M | $D_U$ | 0.02 | 0.02 | 0.04 |
| | $D_{Pu}$ | 0.0015 | 0.0012 | 0.0033 |
| | $FS_{U/Pu}$ | 13.3 | 16.7 | 12.1 |

This Table shows that the presence of a branching in the alkyl group represented by R in above formula (I) leads to compounds having an excellent U(VI)/Pu(IV) selectivity at low acidity ($FS_{U/Pu}$>13), allowing a selective stripping of plutonium from a weakly acidic aqueous phase such as conventionally used at the U/Pu partitioning step, without having to reduce the plutonium.

The distribution coefficients $D_U$ and $D_{Pu}$ are slightly lower than those obtained with MOEHA, notably due to the steric hindrance brought by the branching. These distribution coefficients can nevertheless be strongly increased by increasing the content of extractant. When considering the formation of a $Pu(NO_3)_4L_3$ complex, such as evidenced in foregoing Example II.2 with MOEHA, an increase of the content of M(2-EH)EHA from 0.5 mol/L to 1.5 mol/L would allow an increase in the distribution coefficient of plutonium by a factor of 27, i.e. from 0.056 to 1.5, with 4 moles/L of $HNO_3$, a value that is sufficient in a process to co-extract plutonium under strong acidity.

Figure 2:
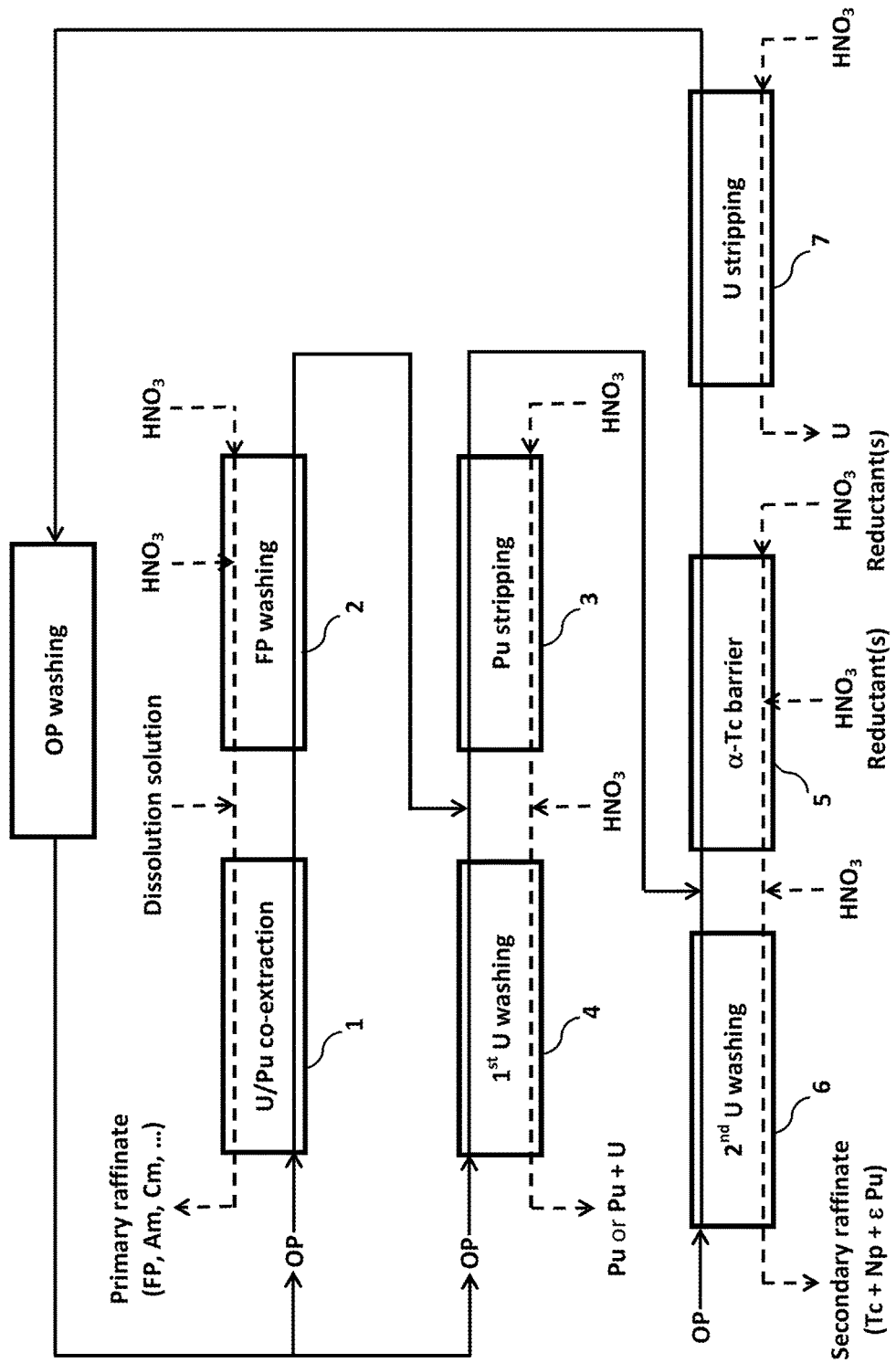
FIG. 2 gives a flow diagram of the method of the invention for processing an aqueous nitric solution resulting from the dissolution of spent nuclear fuel; in this Figure, rectangles 1 to 7 represent multi-stage extractors such as those conventionally used for the processing of spent nuclear fuel (mixer-settlers, pulsed columns or centrifugal extractors); the organic phases are symbolised by solid lines whilst the aqueous phases are symbolised by dotted lines.

III—Flow Diagram of the Method of the Invention for Processing an Aqueous Nitric Solution Resulting from Dissolving a Spent Nuclear Fuel Reference is made to FIG. 2 illustrating a flow diagram of the method of the invention to reprocess an aqueous nitric solution resulting from dissolution of spent nuclear fuel.

As shown in this Figure, the method comprises 8 steps.

The first of these steps, denoted «U/Pu co-extraction» in FIG. 2, is intended to obtain the joint extraction of uranium and plutonium, the first in oxidation state +VI and the second in oxidation state +IV, from the aqueous nitric solution resulting from the dissolution of a spent nuclear fuel.

Such a solution typically comprises from 3 to 6 mol/L of $HNO_3$, uranium, plutonium, minor actinides (americium, curium and neptunium), fission products (La, Ce, Pr, Nd, Sm, Eu, Gd, Mo, Zr, Ru, Tc, Rh, Pd, Y, Cs, Ba, ... ) and a few corrosion products such as iron.

The «U/Pu co-extraction step» is performed by circulating the dissolution solution in extractor 1, in counter-current to an organic phase (denoted «OP» in FIG. 2) which comprises from 1 mol/L to 2 mol/L and better still from 1.3 mol/L to 1.5 mol/L of an N,N-dialkylamide of the invention, or of a mixture of N,N-dialkylamides of the invention, in solution in an organic diluent.

This organic diluent is an aliphatic, linear or branched hydrocarbon, such as n-dodecane, TPH, the isoparaffinic diluent marketed by TOTAL under the trade name Isane IP185T, preference being given to TPH.

The second step of the method, denoted «FP washing» in FIG. 2, is intended to strip the organic phase resulting from «U/Pu co-extraction» of the fraction of fission products that was extracted from the dissolution solution jointly with the uranium and plutonium.

For this purpose, the «FP washing» step comprises one or more washing operations of the organic phase resulting from «U/Pu co-extraction», each washing operation being performed by circulating this organic phase in extractor 2, in counter-current flow to an aqueous nitric solution having a concentration which may range from 0.5 mol/L to 6 mol/L of $HNO_3$, but which is preferably from 4 mol/L to 6 mol/L of $HNO_3$ and better still from 4 to 5 mol/L of $HNO_3$, so as to facilitate the stripping of ruthenium and technetium.

If the «FP washing» step is conducted with one or more aqueous solutions of strong acidity, i.e. typically of 3 mol/L of $HNO_3$ or higher, then this step additionally comprises a de-acidification of the organic phase that is performed by circulating this organic phase in counter-current flow to a weakly acidic aqueous nitric solution, i.e. comprising from 0.1 mol/L to 1 mol/L of $HNO_3$ such as, for example, an aqueous solution comprising 0.5 mol/L of $HNO_3$, to prevent too much acid being carried towards the extractor dedicated to the third step denoted «Pu stripping» in FIG. 2, that would perturb the performance of this third step.

The «Pu stripping» step, which represents the first step of the U/Pu partitioning, is intended to strip the plutonium in oxidation state +IV and therefore without reducing this plutonium, from the organic phase resulting from «FP washing».

This step is performed by circulating this organic phase in extractor 3, in counter-current flow to an aqueous solution comprising from 0.1 mol/L to 0.5 mol/L of $HNO_3$ and by preferably using an O/A flow ratio higher than 1, preferably of 3 or higher and better still of 5 or higher, so that the plutonium(IV) is stripped in concentrating manner.

The stripping of plutonium(IV), performed at the «Pu stripping» step, is accompanied by a stripping of a fraction of uranium(VI) that is also contained in the organic phase resulting from «FP washing».

The fourth step of the method, which is denoted «$1^{st}$ U washing» in FIG. 2 and which corresponds to the second U/Pu partitioning step, is therefore intended to extract from the aqueous phase resulting from «Pu stripping»:

either the entirety of the uranium contained in this aqueous phase if it is desired that the U/Pu partitioning should lead to an aqueous solution comprising plutonium without uranium, and to an organic solution comprising uranium without plutonium;

or the quantity of uranium which, after «$1^{st}$ U washing», allows an aqueous solution to be obtained comprising uranium and plutonium in a previously chosen ratio, if it is desired that the U/Pu partitioning should lead to an aqueous solution comprising a mixture of plutonium and uranium in this ratio, and to an organic solution comprising uranium without plutonium.

In both cases, «$1^{st}$ U washing» is performed by circulating the aqueous phase resulting from «Pu stripping» in extractor 4, in counter-current flow to an organic phase having an identical composition to that of the organic phase used at «U/Pu co-extraction». The quantity of extracted uranium is adjusted by acting firstly on the O/A flow ratio and secondly on the acidity of the aqueous phase, the extraction of uranium being all the greater the higher the organic phase/ aqueous phase flow ratio and the stronger the acidity of the aqueous phase. An addition of $HNO_3$ of greater or lesser concentration to the aqueous phase circulating in extractor 4 can therefore be provided, as a function of the acidity that it is desired to impart to this aqueous phase.

The fifth step denoted «α-Tc barrier» in FIG. 2 is intended to strip, from the organic phase resulting from «Pu stripping», the fraction of technetium that was extracted at «U/Pu co-extraction» but that was not stripped at «FP washing», for the purpose of decontaminating this organic phase with respect to technetium.

It also allows the stripping, from the organic phase resulting from «Pu stripping», of the fraction of neptunium that was extracted at «U/Pu co-extraction» and followed technetium up to «α-Tc barrier», as well as traces of plutonium that this organic phase may still contain.

This step is performed by circulating the organic phase resulting from «Pu stripping» in extractor 5, in counter-current flow to an aqueous nitric solution of low acidity, i.e. comprising from 0.1 mol/L to 3 mol/L of $HNO_3$ and better still 1 mol/L of $HNO_3$, and comprising one or more reducing agents allowing the reduction of technetium—which is contained in the organic phase in oxidation state +VII—to technetium(IV) that is non-extractable by the N,N-dialkylamides, of neptunium(VI) to neptunium(IV) or neptunium (V) that are non-extractable by N,N-dialkylamides under low acidity, and plutonium(IV) to plutonium(III) that is less extractable by N,N-dialkylamides under low acidity than plutonium(IV), without having to reduce uranium(VI).

As reducing agents, the use can therefore be made of uranous nitrate (or U(IV)), hydrazinium nitrate (or NH), hydroxylammonium nitrate (or NHA), acetaldoxime, or a mixture thereof such as a mixture U(IV)/NH, U(IV)/NHA or U(IV)/acetaldoxime, preference being given to a mixture U(IV)/NH or U(VI)/NHA. Gluconic acid can be added to the aqueous solution to reduce phenomena of technetium re-oxidization in the aqueous phase and thereby limit consumption of reducing agent(s).

This step can be conducted at ambient temperature (i.e. 20-25° C.) but preferably it is conducted at a temperature ranging from 30° C. to 40° C. and better still at 32° C. to promote the stripping kinetics of technetium whilst limiting technetium re-oxidization phenomena in the aqueous phase, and hence limit the risk of the technetium, once stripped, of being back-extracted into the organic phase.

The sixth step, denoted «$2^{nd}$ U washing» in FIG. 2 is intended to extract, from the aqueous phase resulting from «α-Tc barrier», the uranium that was stripped together with the technetium at the preceding step, to prevent the «α-Tc barrier» step from resulting in a too high loss of uranium in the aqueous phase.

It is performed by circulating the aqueous phase resulting from «α-Tc barrier» in extractor 6, in counter-current flow to an organic phase having an identical composition to that of the organic phases used for «U/Pu co-extraction» and «$1^{st}$ U washing», after an acidification of this aqueous phase through the addition of concentrated nitric acid, e.g. 10 M, to promote the extraction of uranium.

The seventh step, denoted «U stripping» in FIG. 2, is intended to strip uranium(VI) from the organic phase resulting from «α-Tc barrier».

It is performed by circulating the organic phase resulting from «α-Tc barrier» in extractor 7, in counter-current flow to an aqueous nitric solution of low acidity, i.e. comprising no more than 0.05 mol/L of $HNO_3$ such as, for example, an aqueous solution comprising 0.01 mol/L of $HNO_3$. This step can be performed at ambient temperature (i.e. 20-25° C.) but it is preferably conducted under heat (i.e. typically at a temperature of 40-50° C.) using an O/A flow ratio higher than 1 so that the uranium(VI) is stripped in concentrating manner.

After these 7 steps, we obtain:
- two raffinates, which correspond to the aqueous phases respectively leaving extractors 1 and 6, the first comprising fission products as well as americium and curium («Primary raffinate» in FIG. 2), and the second comprising technetium, neptunium and possibly traces of plutonium («Secondary raffinate» in FIG. 2);
- the aqueous phase leaving extractor 4, which comprises either decontaminated plutonium or a mixture of decontaminated plutonium and decontaminated uranium, called «Pu stream» or «Pu+U stream» accordingly;
- the aqueous phase leaving extractor 7, which comprises decontaminated uranium, called «U stream»; and
- the organic phase leaving extractor 7, which no longer comprises any plutonium or uranium but may contain a certain number of impurities and degradation products (formed by hydrolysis and radiolysis) of the extractant which may have accumulated over the preceding steps.

Therefore, the eighth step, denoted «OP washing» in FIG. 2, is intended to regenerate this organic phase by subjecting it to one or more washes with a basic aqueous solution, for example a first wash with an aqueous solution of 0.3 mol/L of sodium carbonate, followed by a second wash with an aqueous solution of 0.1 mol/L of sodium hydroxide, then one or more washes with an aqueous nitric acid solution allowing a re-acidification thereof, for example an aqueous solution comprising 2 mol/L of $HNO_3$, each wash being performed by circulating said organic phase in an extractor in counter-current flow to the aqueous washing solution.

As can be seen in FIG. 2, the organic phase thus regenerated can be recycled back to extractors 1 and 4 to be re-introduced in the processing cycle.

CITED REFERENCES

[1] FR-A-2 591 213

[2] FR-A-2 642 561

[3] FR-A-2 642 562

[4] Ruikar et al., *Journal of Radioanalytical and Nuclear Chemistry* 1993, 176(2), 103-111

[5] Prabhu et al., *Radiochimica Acta* 1993, 60, 109-114

[6] Cui et al., *Radiochimica Acta* 2005, 93, 287-290

[7] Sun et al., *Journal of Radioanalytical and Nuclear Chemistry* 2005, 264(3), 711-713

What is claimed is:

1. An N,N-dialkylamide of formula (I):

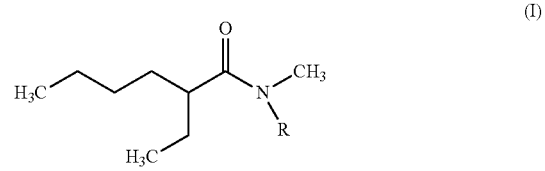

where R is a linear or branched alkyl group having 8 to 15 carbon atoms.

2. The N,N-dialkylamide of claim 1, wherein the alkyl group comprises no more than 12 carbon atoms.

3. The N,N-dialkylamide of claim 2, wherein the alkyl group is an n-octyl, n-decyl, n-dodecyl, 2-ethylhexyl or 2-ethyloctyl group.

4. A method for synthesizing an N,N-dialkylamide of formula (I):

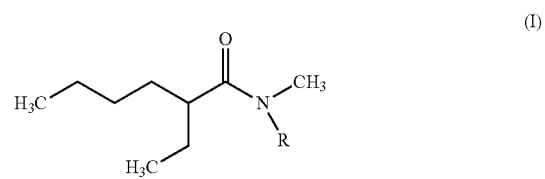

where R is a linear or branched alkyl group having 8 to 15 carbon atoms, comprising a reaction of a halide of formula (II):

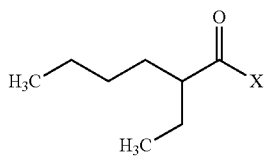

(II)

where X is a halogen atom, with an amine of formula HN(CH$_3$)R where R is a linear or branched alkyl group having 8 to 15 carbon atoms.

5. A method for extracting uranium(VI) and/or plutonium (IV) from an acid aqueous solution, comprising at least one contacting of the acid aqueous solution with an organic solution comprising an N,N-dialkylamide or mixture of N,N-dialkylamides of formula (I):

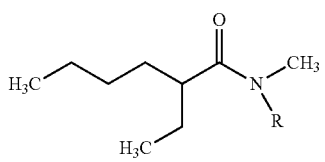

(I)

where R is a linear or branched alkyl group having 8 to 15 carbon atoms, as extractant in an organic diluent, followed by a separation of the aqueous solution from the organic solution.

6. The method of claim 5, wherein the organic solution comprises from 1 mol/L to 2 mol/L of the N,N-dialkylamide or mixture of N,N-dialkylamides.

7. A method for separating totally or partially uranium (VI) from plutonium(IV), uranium(VI) and plutonium(IV) being in an acid aqueous solution, comprising the following steps:
a) a co-extraction of uranium and plutonium from the aqueous solution, the co-extraction comprising at least one contacting of the aqueous solution with an organic solution comprising an N,N-dialkylamide or mixture of N,N-dialkylamides of formula(I):

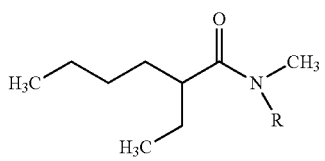

(I)

where R is a linear or branched alkyl group having 8 to 15 carbon atoms, as extractant in solution in an organic diluent, followed by a separation of the aqueous solution from the organic solution;
b) a stripping of plutonium, in oxidation state +IV, and of a fraction of uranium from the organic solution resulting from step a), the stripping comprising at least one contacting of the organic solution with an aqueous solution comprising from 0.1 mol/L to 0.5 mol/L of nitric acid, followed by a separation of the organic solution from the organic solution; and
c) an extraction of all or part of the uranium fraction contained in the aqueous solution resulting from step b), the extraction comprising at least one contacting of the aqueous solution with an organic solution identical to the organic solution of step a), followed by a separation of the aqueous solution from the organic solution;

whereby there are obtained an aqueous solution comprising either plutonium without uranium, or a mixture of plutonium and uranium, and an organic solution comprising uranium without plutonium.

8. The method of claim 7, wherein the organic solution of step a) comprises from 1 mol/L to 2 mol/L of the N,N-dialkylamide or mixture of N,N-dialkylamides.

9. The method of claims 7, wherein the acid aqueous solution is an aqueous solution resulting from a dissolution of a spent nuclear fuel in nitric acid.

10. A single-cycle method for processing an aqueous solution resulting from a dissolution of a spent nuclear fuel in nitric acid, the aqueous solution comprising uranium, plutonium, americium, curium and fission products including technetium, the cycle comprising the following steps:
a) a co-extraction of uranium and plutonium from the aqueous solution, the co-extraction comprising at least one contacting, in an extractor, of the aqueous solution with a first organic solution comprising a N,N-dialkylamide or mixture of N,N-dialkylamides of formula (I):

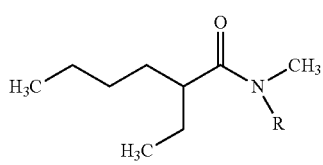

(I)

where R is a linear or branched alkyl group having 8 to 15 carbon atoms, as extractant in solution in an organic diluent, followed by a separation of the aqueous solution from the organic solution;
b) a decontamination of the organic solution resulting from step a) with respect to americium, curium and fission products, the decontamination comprising at least one contacting, in an extractor, of the organic solution with an aqueous solution comprising from 0.5 mol/L to 6 mol/L of nitric acid, followed by a separation of the organic solution from the organic solution;
c) a partitioning of the uranium and plutonium contained in the organic solution resulting from step b) into an aqueous solution comprising either plutonium without uranium, or a mixture of plutonium and uranium, and an organic solution comprising uranium without plutonium, the partitioning comprising:
c$_1$) a stripping of plutonium, in oxidation state +IV, and of a fraction of uranium from the organic solution resulting from step b), the stripping comprising at least one contacting, in an extractor, of the organic solution with an aqueous solution comprising from 0.1 mol/L to 0.5 mol/L of nitric acid, followed by a separation of the organic solution from the organic solution;
c$_2$) an extraction of all or part of the uranium fraction contained in the aqueous solution resulting from c$_1$), the extraction comprising at least one contacting, in an extractor, of the aqueous solution with a second organic solution identical to the organic solution of step a), followed by a separation of the aqueous solution from the organic solution;

d) a decontamination of the organic solution resulting from $c_1$) with respect to technetium, the decontamination comprising:
  $d_1$) a stripping of technetium, in oxidation state +IV, from the organic solution resulting from $c_1$), the stripping comprising at least one contacting, in an extractor, of the organic solution with an aqueous solution comprising from 0.1 mol/L to 3 mol/L of nitric acid and at least one reducing agent capable of reducing technetium from oxidation state +VII to oxidation state +IV, followed by a separation of the organic solution from the organic solution;
  $d_2$) an extraction of the uranium fraction contained in the aqueous solution resulting from $d_1$), the extraction comprising at least one contacting, in an extractor, of the aqueous solution with an organic solution identical to the organic solution of a), followed by a separation of the aqueous solution from the organic solution;
e) a stripping of uranium from the organic solution resulting from $d_1$), the stripping comprising at least one contacting, in an extractor, of the organic solution with an aqueous solution comprising no more than 0.05 mol/L of nitric acid, followed by a separation of the organic solution from the organic solution; and
f) a regeneration of the organic solution resulting from step e); whereby a first and a second aqueous solution are obtained, decontaminated with respect to americium, curium and fission products including technetium, the first aqueous solution comprising either plutonium without uranium, or a mixture of plutonium and uranium, and the second aqueous solution comprising uranium without plutonium.

11. The method of claim 10, wherein the organic solution of step a) comprises from 1 mol/L to 2 mol/L of the N,N-dialkylamide or mixture of N,N-dialkylamides.

12. The method of claim 10, wherein the aqueous solution of step b) comprises from 4 mol/L to 6 mol/L of nitric acid.

13. The method of claim 12, wherein step b) further comprises a de-acidification of the organic solution, the de-acidification comprising at least one contacting of the organic solution with an aqueous solution comprising from 0.1 mol/L to 1 mol/L of nitric acid, followed by a separation of the organic and aqueous solutions.

14. The method of claim 10, wherein the contacting of the organic and aqueous solutions in the extractor of $c_1$) comprises a circulation of the organic and aqueous solutions with a ratio of the flow of organic solution to the flow of aqueous solution higher than 1.

15. The method of claim 10, wherein the reducing agent is uranous nitrate, hydrazinium nitrate, hydroxylammonium nitrate, acetaldoxime or a mixture thereof.

16. The method of claim 10, wherein the extractor of $d_1$) is heated to a temperature of 30° C. to 40° C.

17. The method of claim 10, wherein $d_2$) comprises an acidification of the aqueous solution resulting from $d_1$), to bring a concentration of nitric acid in the aqueous solution to a value of at least 2.5 mol/L, the acidification comprising an adding of nitric acid to the extractor of $d_2$).

18. The method of claim 10, wherein the extractor of step e) is heated to a temperature of 40° C. to 50° C.

19. The method of claim 10, wherein the contacting of the organic and aqueous solutions in the extractor of step e) comprises a circulation of the organic and aqueous solutions with a ratio of the flow of organic solution to the flow of aqueous solution higher than 1.

20. The method of claim 10, wherein the organic solution resulting from step f) is divided into a first and a second fraction, the first fraction forming the first organic solution of step a) and the second fraction forming the second organic solution of $c_2$).

* * * * *